United States Patent [19]
Zeeh et al.

[11] Patent Number: 4,761,486
[45] Date of Patent: Aug. 2, 1988

[54] CYCLOHEXENONE DERIVATIVES, THE PREPARATION AND USE THEREOF AS HERBICIDES AND PLANT GROWTH REGULATORS

[75] Inventors: Bernd Zeeh, Limburgerhof; Dieter Jahn, Edingen-Neckarhausen; Michael Keil, Freinsheim; Dieter Kolassa, Ludwigshafen; Bruno Wuerzer, Otterstadt; Norbert Meyer, Ladenburg; Wilhelm Rademacher; Johann Jung, both of Limburgerhof, all of Fed. Rep. of Germany

[73] Assignee: BASF Aktiengesellschaft, Patentabteilung, Ludwigshafen, Fed. Rep. of Germany

[21] Appl. No.: 3,148

[22] Filed: Jan. 14, 1987

[30] Foreign Application Priority Data

Jan. 16, 1986 [DE] Fed. Rep. of Germany ....... 3601066

[51] Int. Cl.$^4$ ................ C07D 333/22; C07D 337/00; C07D 335/00
[52] U.S. Cl. ........................................ 549/9; 549/11; 549/13; 549/18; 549/19; 549/20; 549/22; 549/34; 549/39; 549/74; 549/75; 549/76; 549/77; 549/79; 549/80; 71/121; 71/123; 71/88; 71/92; 71/94; 71/95; 71/90
[58] Field of Search ............... 549/9, 11, 13, 18, 19, 549/20, 22, 34, 39, 74, 76, 75, 77, 79, 80; 71/121, 123; 568/346, 364

[56] References Cited

U.S. PATENT DOCUMENTS

| | | | |
|---|---|---|---|
| 3,652,770 | 3/1972 | Rohr et al. | 71/121 |
| 3,892,773 | 7/1975 | Allais et al. | 549/13 |
| 3,914,300 | 10/1975 | Haddock et al. | 71/121 |
| 4,422,864 | 12/1983 | Becker et al. | 549/13 |
| 4,463,177 | 7/1984 | Shepherd | 549/13 |
| 4,596,877 | 6/1986 | Becker et al. | 549/13 |
| 4,604,128 | 8/1986 | Watson et al. | 71/121 |
| 4,624,696 | 11/1986 | Keil et al. | 549/13 |
| 4,639,267 | 1/1987 | Farguharson et al. | 71/121 |
| 4,650,513 | 3/1987 | Becker et al. | 549/13 |
| 4,654,073 | 3/1987 | Jahn et al. | 549/13 |

FOREIGN PATENT DOCUMENTS

| | | | |
|---|---|---|---|
| 2755481 | 6/1978 | Fed. Rep. of Germany | 71/121 |
| 53-90248 | 8/1978 | Japan | 71/123 |

*Primary Examiner*—Glennon H. Hollrah
*Assistant Examiner*—Raymond Covington
*Attorney, Agent, or Firm*—Keil & Weinkauf

[57] ABSTRACT

Cyclohexenone derivatives of the formula

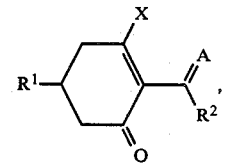

where $R^1$, $R^2$, A and X have the meanings given in the disclosure, a process for their manufacture, herbicidal and plant growth-regulating agents containing the novel active ingredients, and methods of combating unwanted plant growth and of regulating plant growth.

1 Claim, No Drawings

CYCLOHEXENONE DERIVATIVES, THE PREPARATION AND USE THEREOF AS HERBICIDES AND PLANT GROWTH REGULATORS

The present invention relates to novel cyclohexenone derivatives, to a process for their preparation, to herbicidal and plant growth regulating agents which contain the novel active ingredients, and to processes for combating undesirable plant growth and for regulating plant growth.

The herbicidal action of cyclohexenone derivatives which contain in the side chain an oxime ether group in the 2-position is known (DE-A-2,822,304; DE-A-3,227,389; Adv. Pest. Science, Part 2, Pergamon Press, Zurich, 1978; E. H. Geissbühler, Proc. 4th Inter. Congress of Pesticide Chemistry (IUPAC), 1978, 235).

It is further known that certain 2-acyl-3-hydroxycyclohex-2-en-1-ones have a regulating effect on plant growth (EP-A-123 001, EP-A-126,713).

We have found novel cyclohexenone derivatives of the formula I

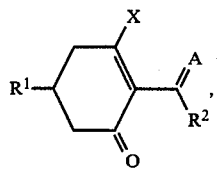

where
$R^1$ is a 5-, 6- or 7-membered heterocycle of 1, 2 or 3 identical or different hetero atoms or ring members selected from the group consisting of N, O, S, SO and $SO_2$, which may contain 1, 2 or 3 double bonds and up to 3 substituents selected from the group consisting of $C_1$–$C_6$-alkyl, $C_2$–$C_6$-alkenyl, $C_1$–$C_6$-alkoxy, $C_1$–$C_6$-alkylthio, $C_1$–$C_4$-dialkylamino and $C_2$–$C_8$-alkoxyalkyl, or is 2-ethylthiopropyl or $C_1$–$C_6$-alkoxycarbonyl, $R^2$ is $C_1$–$C_4$-alkyl, A is oxygen or $NOR^3$, where $R^3$ is $C_1$–$C_4$-alkyl, $C_3$–$C_4$-alkenyl, $C_3$-alkynyl, $C_4$-alkynyl, $C_2$–$C_4$-haloalkyl, $C_3$–$C_4$-haloalkenyl or $C_2$–$C_4$-alkoxyalkyl, and X is halogen, amino, $C_1$–$C_4$-alkylamino, $C_1$–$C_4$-dialkylamino, phenylamino, pyrrolidino, piperidino, morpholino, hexamethyleneimino, $C_1$–$C_4$-alkylthio, phenylthio or an azole selected from the group consisting of pyrrole, pyrazole, imidazole and 1,2,4-triazole, which is bonded to the cyclohexane ring via a nitrogen atom.

Cyclohexenone derivatives of the formula I where A is $NOR^3$ have an advantageous herbicidal action against species of the genus of grasses (Gramineae).

Those cyclohexenone derivatives of the formula I where A is oxygen have advantageous growth regulator properties.

$R^1$ in the formula I is, for example, tetrahydropyran-2-yl, tetrahydropyran-3-yl, 6-methoxytetrahydropyran-2-yl, 6-methoxytetrahydropyran-3-yl, tetrahydropyran-4-yl, 4-methyltetrahydropyran-3-yl, 3-methyltetrahydropyran-4-yl, tetrahydrothiopyran-2-yl, tetrahydrothiopyran-2-yl, tetrahydrothiopyran-3-yl, tetrahydrothiopyran-2-yl, tetrahydrothiopyran-3-yl, $\Delta^3$-dihydrothiopyran-3-yl, tetrahydrofuran-3-yl, 1-oxotetrahydrothiopyran-3-yl, 1,1-dioxotetrahydrothiopyran-3-yl, tetrahydrothien-3-yl, 2,2-dimethyltetrahydrothien-3-yl, pyrid-2-yl, pyrid-3-yl, 2-isopropyl-1,3-dioxepan-5-yl, tetrahydrofuran-2-yl, tetrahydrofuran-3-yl, 1,1-dioxo-2,2-dimethyltetrahydrothien-3-yl, fur-2-yl, 2-methylfur-5-yl, fur-3-yl, thien-2-yl, 1-methylpyrrol-2-yl, 1-methylpyrazol-4-yl, 3-phenylisoxazol-5-yl, 4-methylisothiazol-5-yl, 2-methylthiazol-5-yl, 2-dimethylaminothiazol-5-yl, 5,5-dimethyl-1,3-dioxan-2-yl, isothiazol-5-yl, 4-methylisothiazol-5-yl, 2-ethylthiopropyl or ethoxycarbonyl.

$R^2$ in the formula I is, for example, methyl, ethyl, propyl, isopropyl, butyl, sec-butyl, isobutyl or tert.-butyl.

When A in the formula I is $NOR^3$, $R^3$ is, for example, methyl, ethyl, propyl, allyl, (E)-but-2-en-1-yl, propargyl, 2-chloroethyl, (E)-3-chloropropen-1-yl, methoxymethyl or methoxyethyl.

X in the formula I is, for example, fluorine, chlorine, bromine, amino, methylamino, isopropylamino, dimethylamino, diethylamino, phenylamino, pyrrolidino, piperidino, morpholino, hexamethyleneimino, anilino, methylthio, ethylthio, propylthio, phenylthio, pyrrol-1-yl, pyrazol-1-yl, imidazol-1-yl or 1,2,4-triazol-1-yl.

Preference is given to cyclohexanone derivatives of the formula I where $R^1$ is tetrahydropyran-3-yl, tetrahydropyran-4-yl or tetrahydrothiopyran-3-yl, $R^2$ is ethyl or propyl and A is oxygen or $NOR^3$ where $R^3$ is ethyl, $C_3$–$C_4$-alkenyl or $C_3$–$C_4$-haloalkenyl.

The novel cyclohexenone derivatives can advantageously be obtained by reacting a compound of the formula II

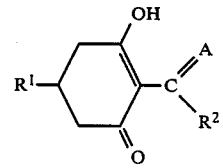

where $R^1$, $R^2$ and A have the abovementioned meanings, first with a chlorinating or brominating agent at from $-10°$ to $+120°$ C., preferably from $20°$ to $80°$ C., in the presence or absence of a base.

Expedient chlorinating or brominating agents are inorganic or organic acid chlorides or bromides, for example thionyl chloride, thionyl bromide, phosgene, phosphorus oxychloride, phosphorusoxybromide, phosphorus pentachloride, phosphorus pentabromide or oxalyl chloride.

Suitable bases are tertiary amine bases, such as triethylamine, N,N-dimethylaminocyclohexane or pyridine.

Tricarbonyl compounds and halogenating agents are used in a molar ratio of from 1:1 to 1:20.

If the reaction is carried out in the presence of a base, the base is used in an amount of from 1 to 20 moles per mole of tricarbonyl compound.

In some cases it can be of advantage to carry out the reaction in the presence of an inert solvent, for example benzene, toluene, chloroform, dichloromethane, 1,2-dichloroethane, dioxane, tetrahyrofuran, N,N-dimethylformamide or N-methylpyrrolidone.

The reaction is complete after a few hours. The target product of the formula I where X is chlorine or bromine is obtained by concentrating the reaction mixture.

Those compounds of the formula I where X has a meaning other than chlorine or bromine are obtained by reacting the particular chlorine or bromine compound with a nucleophile of the formula X-H, where X has the abovementioned meanings other than chlorine or bromine, at from $-10°$ to $+120°$ C.

If desired, this reaction is carried out in the presence of a tertiary amine base, for example triethylamine, N,N-dimethylaminocyclohexane or pyridine.

If a fluorine atom is to be incorporated into the cyclohexane ring it is advisable not to use free hydrogen fluoride but first to convert the hydrogen fluoride into a fluoride salt, or to use a fluoride from the start.

The chlorine or bromine compound and the nucleophile (X-H) are used in molar ratio of from 1:1 to 1:20. If the reaction is carried out in the presence of a base, the base is used in an amount of from 1 to 20 moles per mole of the chlorine or bromine compound.

The substitution reaction can also be carried out in the presence of an inert solvent, for example benzene, toluene, chloroform, dichloromethane, 1,2-dichloroethane, dioxane, tetrahydrofuran, N,N-dimethylformamide or N-methylpyrrolidone.

The reaction is complete after a few hours, when the reaction product can be obtained by concentrating the reaction solution, taking up in methylene chloride and extracting with dilute sodium carbonate solution and water. After removal of the solvent the crude products thus obtained can be purified by column chromatography over silica gel.

The compounds of the formula II are known and are described in example in DE-A-3,121,355, DE-A-2,822,304 and EP-A-123,001.

The invention is explained in more detail by the following Examples.

EXAMPLE 1

420 ml of oxalyl chloride were added at 0° to 5° C. to 141.2 g (0.5 mol) of 2-butyryl-3-hydroxy-5-(tetrahydrothiopyran-3-yl)cyclohex-2-en-1-one, and the mixture was stirred at room temperature for 16 hours and concentrated. The oil obtained was treated with methyl tert.-butyl ether, and the resulting solid was filtered off with suction and dried. This gave 125.9 g (84% yield) of 2-butyryl-3-chloro-5-(tetrahydrothiopyran-3-yl)cyclohex-2-en-1-one having a melting point of 97° C. (decomposition) (compound no. 312).

EXAMPLE 2

10.0 g (31 mmol) of 2-(1-ethoxyiminobutyl-3-hydroxy-5-(tetrahydrothiopyran-3-yl)cyclohex-2-en-1-one were dissolved in 50 ml of tetrahydrofuran, and 4.7 ml of triethylamine were added, followed by 2.3 ml of thionyl chloride. After 3 hours the resulting precipitate was filtered off with suction, and washed with tetrahydrofuran, and the product-containing filtrate was concentrated. 3-Chloro-2-(1-ethoxyiminobutyl)-5-(tetrahydrothiopyran-3-yl)cyclohex-2-en-1-one was obtained as an oil (compound no. 90).

EXAMPLE 3

A solution of 4.5 ml (50 mmol) of propanethiol, 125 ml of tetrahydrofuran, 7 ml of triethylamine and 15.0 g (50 mmol) of 2-butyryl-3-chloro-5-(tetrahydrothiopyran)cyclohex-2-en-1-one was refluxed for 4 hours, the resulting precipitate was filtered off, and the filtrate was concentrated. The residue obtained was taken up in 300 ml of dichloromethane, extracted twice with 200 ml of water each time and dried over sodium sulfate. Concentrating gave 6.6 g of 2-butyryl-3-propylthio-5-(tetrahydrothiopyran-3-yl)cyclohex-2-en-1-one in the form of an oil (compound no. 323).

EXAMPLE 4

A solution of 10.0 g (33 mmol) of 2-butyryl-3-chloro-5-(tetrahydrothiopyran-3-yl)cyclohex-2-en-1-one in 80 ml of N,N-dimethylformamide was added dropwise to a solution of 6.8 g (0.1 mol) of pyrazole in 100 ml of N,N-dimethylformamide. After 4 hours of stirring, the mixture was concentrated, and the residue obtained was chromatographed over silica gel. This gave 7.3 g of 2-butyryl-3-(pyrazol-1-yl)-5-(tetrahydrothiopyran-3-yl)cyclohex-2-en-1-one having a melting point of 127° C. (compound no. 325).

EXAMPLE 5

10.3 g (30 mmol) of 3-chloro-2-(1-ethoxyiminobutyl)-5-(tetrahydrothiopyran-3-yl)cyclohex-2-en-1-one, 5.1 ml (60 mmol) of isopropylamine and 100 ml of toluene were stirred at 60° C. for 6 hours. After cooling down, the mixture was extracted three times with 75 ml of water each time, dried over sodium sulfate and concentrated. The residue thus obtained was chromatographed over silica gel. This gave 3.8 g of 2-ethoxyimino-3-isopropylamino-5-(tetrahydrothiopyran-3-yl)cyclohex-2-en-1-one having a melting point of 104° C. (compound no. 103).

The compounds listed in Tables 1 and 2 below can be obtained in a similar manner.

TABLE 1

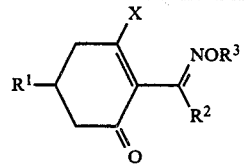

(Ib)

| Compound no. | $R^1$ | $R^2$ | $R^3$ | X |
|---|---|---|---|---|
| 1 | tetrahydrofuran-2-yl | ethyl | $C_2H_5$ | Cl |
| 2 | tetrahydrofuran-2-yl | propyl | $C_2H_5$ | Cl |
| 3 | tetrahydrofuran-3-yl | ethyl | $C_2H_5$ | Cl |
| 4 | tetrahydrofuran-3-yl | propyl | $C_2H_5$ | Cl |
| 5 | tetrahydrofuran-3-yl | propyl | $C_2H_5$ | $NH_2$ |
| 6 | tetrahydrofuran-3-yl | propyl | $C_2H_5$ | $NHCH_3$ |
| 7 | tetrahydrofuran-3-yl | propyl | $C_2H_5$ | 1-pyrazolyl |
| 8 | tetrahydrofuran-3-yl | propyl | $C_2H_5$ | $C_2H_5$ |
| 9 | tetrahydrothien-3-yl | ethyl | $C_2H_5$ | Cl |
| 10 | tetrahydrothien-3-yl | propyl | $C_2H_5$ | Cl |
| 11 | 2,2-dimethyl-2,5-dihydrothien-3-yl | ethyl | $C_2H_5$ | Cl |
| 12 | 2,2-dimethyl-2,5-dihydrothien-3-yl | propyl | $C_2H_5$ | Cl |
| 13 | 2-furyl | ethyl | $C_2H_5$ | Cl |

TABLE 1-continued

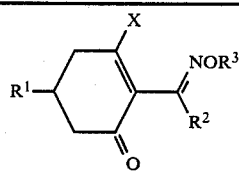

(Ib)

| Compound no. | R¹ | R² | R³ | X |
|---|---|---|---|---|
| 14 | 2-furyl | propyl | $C_2H_5$ | Cl |
| 15 | 2-furyl | propyl | $C_2H_5$ | $NH_2$ |
| 16 | 2-furyl | propyl | $C_2H_5$ | 1-pyrrolidinyl |
| 17 | 2-furyl | propyl | $C_2H_5$ | N—morpholino |
| 18 | 2-furyl | propyl | $C_2H_5$ | phenylamino |
| 19 | 2-furyl | ethyl | $C_2H_5$ | Cl |
| 20 | 2-furyl | propyl | $C_2H_5$ | Cl |
| 21 | 2-thienyl | ethyl | $C_2H_5$ | Cl |
| 22 | 2-thienyl | propyl | $C_2H_5$ | Cl |
| 23 | 3-thienyl | ethyl | $C_2H_5$ | Cl |
| 24 | 3-thienyl | propyl | $C_2H_5$ | Cl |
| 25 | 2,5-dimethyl-thien-3-yl | ethyl | $C_2H_5$ | Cl |
| 26 | 2,5-dimethyl-thien-3-yl | propyl | $C_2H_5$ | Cl |
| 27 | 3-methyl-isoxazol-5-yl | ethyl | $C_2H_5$ | Cl |
| 28 | 3-methyl-isoxazol-5-yl | propyl | $C_2H_5$ | Cl |
| 29 | 3-isopropyl-isoxazol-5-yl | ethyl | $C_2H_5$ | Cl |
| 30 | 3-isopropyl-isoxazol-5-yl | propyl | $C_2H_5$ | Cl |
| 31 | 4-methyl-isothiazol-5-yl | ethyl | $C_2H_5$ | Cl |
| 32 | 4-methyl-isothiazol-5-yl | propyl | $C_2H_5$ | Cl |
| 33 | isothiazol-4-yl | ethyl | $C_2H_5$ | Cl |
| 34 | isothiazol-4-yl | propyl | $C_2H_5$ | Cl |
| 35 | 2-methyl-thiazol-4-yl | ethyl | $C_2H_5$ | Cl |
| 36 | 2-methxyl-thiazol-4-yl | propyl | $C_2H_5$ | Cl |
| 37 | 2-methyl-thiazol-5-yl | ethyl | $C_2H_5$ | Cl |
| 38 | 2-methyl-thiazol-5-yl | propyl | $C_2H_5$ | Cl |
| 39 | 2-phenyl-thiazol-4-yl | ethyl | $C_2H_5$ | Cl |
| 40 | tetrahydropyran-2-yl | ethyl | $C_2H_5$ | Cl |
| 41 | tetrahydropyran-2-yl | propyl | $C_2H_5$ | Cl |
| 42 | 6-methyl-tetrahydropyran-2-yl | ethyl | $C_2H_5$ | Cl |
| 43 | 6-methyl-tetrahydropyran-2-yl | propyl | $C_2H_5$ | Cl |
| 44 | 6-methoxy-tetrahydropyran-2-yl | ethyl | $C_2H_5$ | Cl |
| 45 | 6-methoxy-tetrahydropyran-2-yl | propyl | $C_2H_5$ | Cl |
| 46 | 6-Ethoxy-tetrahydropyran-2-yl | ethyl | $C_2H_5$ | Cl |
| 47 | 6-Ethoxy-tetrahydropyran-2-yl | propyl | $C_2H_5$ | Cl |
| 48 | tetrahydropyran-3-yl | methyl | $C_2H_5$ | Cl |
| 49 | tetrahydropyran-3-yl | methyl | $CH_2$—$CH$=$CH_2$ | Cl |
| 50 | tetrahydropyran-3-yl | methyl | $CH_2$—$CH$=$CH_2$ | $NH_2$ |
| 51 | tetrahydropyran-3-yl | methyl | $CH_2$—$CH$=$CH_2$ | 1-pyrazolyl |
| 52 | tetrahydropyran-3-yl | ethyl | $C_2H_5$ | Cl |
| 53 | tetrahydropyran-3-yl | propyl | $C_2H_5$ | Cl |
| 54 | tetrahydropyran-3-yl | propyl | $C_2H_5$ | $NH_2$ |
| 55 | tetrahydropyran-3-yl | propyl | $C_2H_5$ | $NHCH_3$ |
| 56 | tetrahydropyran-3-yl | propyl | $C_2H_5$ | $C_2H_5S$ |
| 57 | tetrahydropyran-3-yl | propyl | $C_2H_5$ | 1,2,4-triazol-1-yl |
| 58 | tetrahydropyran-3-yl | propyl | $C_2H_5$ | 1-pyrazolyl |
| 59 | tetrahydropyran-3-yl | propyl | $C_2H_5$ | 1-imidazolyl |
| 60 | tetrahydropyran-3-yl | propyl | $C_2H_5$ | N—piperidyl |
| 61 | tetrahydropyran-3-yl | propyl | $C_2H_5$ | N—morpholino |
| 62 | 4-methyl-tetrahydropyran-3-yl | ethyl | $C_2H_5$ | Cl |
| 63 | 4-methyl-tetrahydropyran-3-yl | propyl | $C_2H_5$ | Cl |
| 64 | 2-methoxy-tetrahydropyran-3-yl | ethyl | $C_2H_5$ | Cl |
| 65 | 4-methyl-tetrahydropyran-3-yl | propyl | $C_2H_5$ | Cl |
| 66 | tetrahydropyran-4-yl | methyl | $C_2H_5$ | Cl |
| 67 | tetrahydropyran-4-yl | ethyl | $C_2H_5$ | Cl |
| 68 | tetrahydropyran-4-yl | propyl | $C_2H_5$ | Cl |
| 69 | tetrahydropyran-4-yl | isopropyl | $C_2H_5$ | Cl |
| 70 | tetrahydropyran-4-yl | Butyl | $C_2H_5$ | Cl |
| 71 | tetrahydropyran-4-yl | ethyl | (E)—$CH_2$—$CH$=$CH$—Cl | Cl |
| 72 | tetrahydropyran-4-yl | ethyl | (E)—$CH_2$—$CH$=$CH$—Cl | $NH_2$ |
| 73 | tetrahydropyran-4-yl | ethyl | (E)—$CH_2$—$CH$=$CH$—Cl | $NHCH_3$ |
| 74 | tetrahydropyran-4-yl | ethyl | (E)—$CH_2$—$CH$=$CH$—Cl | $N(CH_3)_2$ |
| 75 | tetrahydropyran-4-yl | ethyl | (E)—$CH_2$—$CH$=$CH$—Cl | phenylamino |
| 76 | tetrahydropyran-4-yl | ethyl | (E)—$CH_2$—$CH$=$CH$—Cl | isopropylamino |
| 77 | tetrahydropyran-4-yl | ethyl | (E)—$CH_2$—$CH$=$CH$—Cl | 1-pyrrolidinyl |
| 78 | tetrahydropyran-4-yl | ethyl | (E)—$CH_2$—$CH$=$CH$—Cl | $C_2H_5S$ |
| 79 | tetrahydropyran-4-yl | ethyl | (E)—$CH_2$—$CH$=$CH$—Cl | 1-pyrazolyl |
| 80 | tetrahydropyran-4-yl | ethyl | (E)—$CH_2$—$CH$=$CH$—Cl | 1,2,4-triazol-1-yl |
| 81 | 3-methyl-tetrahydropyran-4-yl | ethyl | $C_2H_5$ | Cl |
| 82 | 3-methyl-tetrahydropyran-4-yl | propyl | $C_2H_5$ | Cl |
| 83 | $\Delta^3$-dihydropyran-3-yl | ethyl | $C_2H_5$ | Cl |
| 84 | $\Delta^3$-dihydropyran-3-yl | propyl | $C_2H_5$ | Cl |

TABLE 1-continued

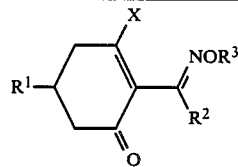
(Ib)

| Compound no. | R¹ | R² | R³ | X |
|---|---|---|---|---|
| 85 | tetrahydrothiopyran-3-yl | methyl | $C_2H_5$ | Cl |
| 86 | tetrahydrothiopyran-3-yl | ethyl | $C_2H_5$ | Cl |
| 87 | tetrahydrothiopyran-3-yl | isopropyl | $C_2H_5$ | Cl |
| 88 | tetrahydrothiopyran-3-yl | Butyl | $C_2H_5$ | Cl |
| 89 | tetrahydrothiopyran-3-yl | isobutyl | $C_2H_5$ | Cl |
| 90 | tetrahydrothiopyran-3-yl | propyl | $C_2H_5$ | Cl |
| 91 | tetrahydrothiopyran-3-yl | isobutyl | $C_2H_5$ | F |
| 92 | tetrahydrothiopyran-3-yl | propyl | $C_2H_5$ | Br |
| 93 | tetrahydrothiopyran-3-yl | propyl | $C_2H_5$ | $NH_2$ |
| 94 | tetrahydrothiopyran-3-yl | propyl | $C_2H_5$ | $NHCH_3$ |
| 95 | tetrahydrothiopyran-3-yl | propyl | $C_2H_5$ | $N(CH_3)_2$ |
| 96 | tetrahydrothiopyran-3-yl | propyl | $C_2H_5$ | $CH_3S$ |
| 97 | tetrahydrothiopyran-3-yl | propyl | $C_2H_5$ | $n\text{-}C_3H_7S$ |
| 98 | tetrahydrothiopyran-3-yl | propyl | $C_2H_5$ | phenylthio |
| 99 | tetrahydrothiopyran-3-yl | propyl | $C_2H_5$ | 1-pyrazolyl |
| 100 | tetrahydrothiopyran-3-yl | propyl | $C_2H_5$ | 1,2,4-triazol-1-yl |
| 101 | tetrahydrothiopyran-3-yl | propyl | $C_2H_5$ | 1-pyrrolidinyl |
| 102 | tetrahydrothiopyran-3-yl | propyl | $C_2H_5$ | N—morpholino |
| 103 | tetrahydrothiopyran-3-yl | propyl | $C_2H_5$ | isopropylamino |
| 104 | tetrahydrothiopyran-3-yl | propyl | $C_2H_5$ | phenylamino |
| 105 | tetrahydrothiopyran-3-yl | propyl | $C_2H_5$ | 1-imidazolyl |
| 106 | tetrahydrothiopyran-3-yl | propyl | $CH_2\text{—}CH\text{=}CH_2$ | Cl |
| 107 | tetrahydrothiopyran-3-yl | propyl | $CH_2\text{—}CH\text{=}CH_2$ | F |
| 108 | tetrahydrothiopyran-3-yl | propyl | $CH_2\text{—}CH\text{=}CH_2$ | Br |
| 109 | tetrahydrothiopyran-3-yl | propyl | $CH_2\text{—}CH\text{=}CH_2$ | $NH_2$ |
| 110 | tetrahydrothiopyran-3-yl | propyl | $CH_2\text{—}CH\text{=}CH_2$ | $NHCH_3$ |
| 111 | tetrahydrothiopyran-3-yl | propyl | $CH_2\text{—}CH\text{=}CH_2$ | $N(CH_3)_2$ |
| 112 | tetrahydrothiopyran-3-yl | propyl | $CH_2\text{—}CH\text{=}CH_2$ | $CH_2S$ |
| 113 | tetrahydrothiopyran-3-yl | propyl | $CH_2\text{—}CH\text{=}CH_2$ | $n\text{-}C_3H_7S$ |
| 114 | tetrahydrothiopyran-3-yl | propyl | $CH_2\text{—}CH\text{=}CH_2$ | phenylthio |
| 115 | tetrahydrothiopyran-3-yl | propyl | $CH_2\text{—}CH\text{=}CH_2$ | 1-pyrazolyl |
| 116 | tetrahydrothiopyran-3-yl | propyl | $CH_2\text{—}CH\text{=}CH_2$ | 1,2,4-triazol-1-yl |
| 117 | tetrahydrothiopyran-3-yl | propyl | $CH_2\text{—}CH\text{=}CH_2$ | 1-pyrrolidinyl |
| 118 | tetrahydrothiopyran-3-yl | propyl | $CH_2\text{—}CH\text{=}CH_2$ | N—morpholino |
| 119 | tetrahydrothiopyran-3-yl | propyl | $CH_2\text{—}CH\text{=}CH_2$ | isopropylamino |
| 120 | tetrahydrothiopyran-3-yl | propyl | $CH_2\text{—}CH\text{=}CH_2$ | phenylamino |
| 121 | tetrahydrothiopyran-3-yl | propyl | $CH_2\text{—}CH\text{=}CH_2$ | 1-imidazolyl |
| 122 | tetrahydrothiopyran-3-yl | propyl | $(E)\text{—}CH_2\text{—}CH\text{=}CH\text{—}CH_3$ | Cl |
| 123 | tetrahydrothiopyran-3-yl | propyl | $(E)\text{—}CH_2\text{—}CH\text{=}CH\text{—}CH_3$ | F |
| 124 | tetrahydrothiopyran-3-yl | propyl | $(E)\text{—}CH_2\text{—}CH\text{=}CH\text{—}CH_3$ | Br |
| 125 | tetrahydrothiopyran-3-yl | propyl | $(E)\text{—}CH_2\text{—}CH\text{=}CH\text{—}CH_3$ | $NH_2$ |
| 126 | tetrahydrothiopyran-3-yl | propyl | $(E)\text{—}CH_2\text{—}CH\text{=}CH\text{—}CH_3$ | $NHCH_3$ |
| 127 | tetrahydrothiopyran-3-yl | propyl | $(E)\text{—}CH_2\text{—}CH\text{=}CH\text{—}CH_3$ | $N(CH_3)_2$ |
| 128 | tetrahydrothiopyran-3-yl | propyl | $(E)\text{—}CH_2\text{—}CH\text{=}CH\text{—}CH_3$ | $CH_3S$ |
| 129 | tetrahydrothiopyran-3-yl | propyl | $(E)\text{—}CH_2\text{—}CH\text{=}CH\text{—}CH_3$ | $n\text{-}C_3H_7S$ |
| 130 | tetrahydrothiopyran-3-yl | propyl | $(E)\text{—}CH_2\text{—}CH\text{=}CH\text{—}CH_3$ | phenylthio |
| 131 | tetrahydrothiopyran-3-yl | propyl | $(E)\text{—}CH_2\text{—}CH\text{=}CH\text{—}CH_3$ | 1-pyrazolyl |
| 132 | tetrahydrothiopyran-3-yl | propyl | $(E)\text{—}CH_2\text{—}CH\text{=}CH\text{—}CH_3$ | 1,2,4-triazol-1-yl |
| 133 | tetrahydrothiopyran-3-yl | propyl | $(E)\text{—}CH_2\text{—}CH\text{=}CH\text{—}CH_3$ | 1-pyrrolidinyl |
| 134 | tetrahydrothiopyran-3-yl | propyl | $(E)\text{—}CH_2\text{—}CH\text{=}CH\text{—}CH_3$ | N—morpholino |
| 135 | tetrahydrothiopyran-3-yl | propyl | $(E)\text{—}CH_2\text{—}CH\text{=}CH\text{—}CH_3$ | isopropylamino |
| 136 | tetrahydrothiopyran-3-yl | propyl | $(E)\text{—}CH_2\text{—}CH\text{=}CH\text{—}CH_3$ | phenylamino |
| 137 | tetrahydrothiopyran-3-yl | propyl | $(E)\text{—}CH_2\text{—}CH\text{=}CH\text{—}CH_3$ | 1-imidazolyl |
| 138 | tetrahydrothiopyran-3-yl | propyl | $(E)\text{—}CH_2\text{—}CH\text{=}CH\text{—}Cl$ | Cl |
| 139 | tetrahydrothiopyran-3-yl | propyl | $(E)\text{—}CH_2\text{—}CH\text{=}CH\text{—}Cl$ | F |
| 140 | tetrahydrothiopyran-3-yl | propyl | $(E)\text{—}CH_2\text{—}CH\text{=}CH\text{—}Cl$ | Br |
| 141 | tetrahydrothiopyran-3-yl | propyl | $(E)\text{—}CH_2\text{—}CH\text{=}CH\text{—}Cl$ | $NH_2$ |
| 142 | tetrahydrothiopyran-3-yl | propyl | $(E)\text{—}CH_2\text{—}CH\text{=}CH\text{—}Cl$ | $NHCH_3$ |
| 143 | tetrahydrothiopyran-3-yl | propyl | $(E)\text{—}CH_2\text{—}CH\text{=}CH\text{—}Cl$ | $N(CH_3)_2$ |
| 144 | tetrahydrothiopyran-3-yl | propyl | $(E)\text{—}CH_2\text{—}CH\text{=}CH\text{—}Cl$ | $CH_3S$ |
| 145 | tetrahydrothiopyran-3-yl | propyl | $(E)\text{—}CH_2\text{—}CH\text{=}CH\text{—}Cl$ | $n\text{-}C_3H_7S$ |
| 146 | tetrahydrothiopyran-3-yl | propyl | $(E)\text{—}CH_2\text{—}CH\text{=}CH\text{—}Cl$ | phenylthio |
| 147 | tetrahydrothiopyran-3-yl | propyl | $(E)\text{—}CH_2\text{—}CH\text{=}CH\text{—}Cl$ | 1-pyrazolyl |
| 148 | tetrahydrothiopyran-3-yl | propyl | $(E)\text{—}CH_2\text{—}CH\text{=}CH\text{—}Cl$ | 1,2,4-triazol-1-yl |
| 149 | tetrahydrothiopyran-3-yl | propyl | $(E)\text{—}CH_2\text{—}CH\text{=}CH\text{—}Cl$ | 1-pyrrolidinyl |
| 150 | tetrahydrothiopyran-3-yl | propyl | $(E)\text{—}CH_2\text{—}CH\text{=}CH\text{—}Cl$ | N—morpholino |
| 151 | tetrahydrothiopyran-3-yl | propyl | $(E)\text{—}CH_2\text{—}CH\text{=}CH\text{—}Cl$ | isopropylamino |
| 152 | tetrahydrothiopyran-3-yl | propyl | $(E)\text{—}CH_2\text{—}CH\text{=}CH\text{—}Cl$ | phenylamino |
| 153 | tetrahydrothiopyran-3-yl | propyl | $(E)\text{—}CH_2\text{—}CH\text{=}CH\text{—}Cl$ | 1-imidazolyl |
| 154 | tetrahydrothiopyran-3-yl | propyl | $CH_2\text{—}CH_2Cl$ | Cl |
| 155 | tetrahydrothiopyran-3-yl | propyl | $CH_2\text{—}CH_2Cl$ | F |

TABLE 1-continued

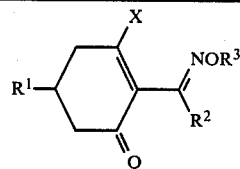
(Ib)

| Compound no. | R¹ | R² | R³ | X |
|---|---|---|---|---|
| 156 | tetrahydrothiopyran-3-yl | propyl | $CH_2-CH_2Cl$ | Br |
| 157 | tetrahydrothiopyran-3-yl | propyl | $CH_2-CH_2Cl$ | $NH_2$ |
| 158 | tetrahydrothiopyran-3-yl | propyl | $CH_2-CH_2Cl$ | $NHCH_3$ |
| 159 | tetrahydrothiopyran-3-yl | propyl | $CH_2-CH_2Cl$ | $N(CH_3)_2$ |
| 160 | tetrahydrothiopyran-3-yl | propyl | $CH_2-CH_2Cl$ | $CH_3S$ |
| 161 | tetrahydrothiopyran-3-yl | propyl | $CH_2-CH_2Cl$ | $n-C_3H_7S$ |
| 162 | tetrahydrothiopyran-3-yl | propyl | $CH_2-CH_2Cl$ | phenylthio |
| 163 | tetrahydrothiopyran-3-yl | propyl | $CH_2-CH_2Cl$ | 1-pyrazolyl |
| 164 | tetrahydrothiopyran-3-yl | propyl | $CH_2-CH_2Cl$ | 1,2,4-triazol-1-yl |
| 165 | tetrahydrothiopyran-3-yl | propyl | $CH_2-CH_2Cl$ | 1-pyrrolidinyl |
| 166 | tetrahydrothiopyran-3-yl | propyl | $CH_2-CH_2Cl$ | N—morpholino |
| 167 | tetrahydrothiopyran-3-yl | propyl | $CH_2-CH_2Cl$ | isopropylamino |
| 168 | tetrahydrothiopyran-3-yl | propyl | $CH_2-CH_2Cl$ | phenylamino |
| 169 | tetrahydrothiopyran-3-yl | propyl | $CH_2-CH_2Cl$ | 1-imidazoyl |
| 170 | tetrahydrothiopyran-3-yl | propyl | $CH_2-C{\equiv}CH$ | Cl |
| 171 | tetrahydrothiopyran-3-yl | propyl | $CH_2-C{\equiv}CH$ | F |
| 172 | tetrahydrothiopyran-3-yl | propyl | $CH_2-C{\equiv}CH$ | Br |
| 173 | tetrahydrothiopyran-3-yl | propyl | $CH_2-C{\equiv}CH$ | $NH_2$ |
| 174 | tetrahydrothiopyran-3-yl | propyl | $CH_2-C{\equiv}CH$ | $NHCH_3$ |
| 175 | tetrahydrothiopyran-3-yl | propyl | $CH_2-C{\equiv}CH$ | $N(CH_3)_2$ |
| 176 | tetrahydrothiopyran-3-yl | propyl | $CH_2-C{\equiv}CH$ | $CH_3S$ |
| 177 | tetrahydrothiopyran-3-yl | propyl | $CH_2-C{\equiv}CH$ | $n-C_3H_7S$ |
| 178 | tetrahydrothiopyran-3-yl | propyl | $CH_2-C{\equiv}CH$ | phenylthio |
| 179 | tetrahydrothiopyran-3-yl | propyl | $CH_2-C{\equiv}CH$ | 1-pyrazolyl |
| 180 | tetrahydrothiopyran-3-yl | propyl | $CH_2-C{\equiv}CH$ | 1,2,4-triazol-1-yl |
| 181 | tetrahydrothiopyran-3-yl | propyl | $CH_2-C{\equiv}CH$ | 1-pyrrolidinyl |
| 182 | tetrahydrothiopyran-3-yl | propyl | $CH_2-C{\equiv}CH$ | N—morpholino |
| 183 | tetrahydrothiopyran-3-yl | propyl | $CH_2-C{\equiv}CH$ | isopropylamino |
| 184 | tetrahydrothiopyran-3-yl | propyl | $CH_2-C{\equiv}CH$ | phenylamino |
| 185 | tetrahydrothiopyran-3-yl | propyl | $CH_2-C{\equiv}CH$ | 1-imidazolyl |
| 186 | 1-oxo-tetrahydrothiopyran-3-yl | ethyl | $C_2H_5$ | Cl |
| 187 | 1-oxo-tetrahydrothiopyran-3-yl | propyl | $C_2H_5$ | Cl |
| 188 | 1,1-dioxo-tetrahydrothiopyran-3-yl | ethyl | $C_2H_5$ | Cl |
| 189 | 1,1-dioxo-tetrahydrothiopyran-3-yl | propyl | $C_2H_5$ | Cl |
| 190 | tetrahydrothiopyran-4-yl | ethyl | $C_2H_5$ | Cl |
| 191 | tetrahydrothiopyran-4-yl | propyl | $C_2H_5$ | Cl |
| 192 | Δ³-dihydrothiopyran-3-yl | ethyl | $C_2H_5$ | Cl |
| 193 | Δ³-dihydrothiopyran-3-yl | propyl | $C_2H_5$ | Cl |
| 194 | 5,5-dimethyl-1,3-dioxan-2-yl | ethyl | $C_2H_5$ | Cl |
| 195 | 5,5-dimethyl-1,3-dioxan-2-yl | propyl | $C_2H_5$ | Cl |
| 196 | 1,4-dioxan-2-yl | ethyl | $C_2H_5$ | Cl |
| 197 | 1,4-dioxan-2-yl | propyl | $C_2H_5$ | Cl |
| 198 | 1,4-dithian-2-yl | ethyl | $C_2H_5$ | Cl |
| 199 | 1,4-dithian-2-yl | propyl | $C_2H_5$ | Cl |
| 200 | 2-pyridyl | ethyl | $C_2H_5$ | Cl |
| 201 | 2-pyridyl | propyl | $C_2H_5$ | Cl |
| 202 | 3-pyridyl | ethyl | $C_2H_5$ | Cl |
| 203 | 3-pyridyl | propyl | $C_2H_5$ | Cl |
| 204 | 3-pyridyl | propyl | $C_2H_5$ | $NH_2$ |
| 205 | 3-pyridyl | propyl | $C_2H_5$ | $N(CH_3)_2$ |
| 206 | 3-pyridyl | propyl | $C_2H_5$ | 1-pyrazolyl |
| 207 | 3-pyridyl | propyl | $C_2H_5$ | 1,2,4-triazol-1-yl |
| 208 | 1,3-dioxepan-5-yl | ethyl | $C_2H_5$ | Cl |
| 209 | 1,3-dioxepan-5-yl | propyl | $C_2H_5$ | Cl |
| 210 | 2-methyl-1,3-dioxepan-5-yl | ethyl | $C_2H_5$ | Cl |
| 211 | 2-methyl-1,3-dioxepan-5-yl | propyl | $C_2H_5$ | Cl |
| 212 | 2-isopropyl-1,3-dioxepan-5-yl | ethyl | $C_2H_5$ | Cl |
| 213 | 2-isopropyl-1,3-dioxepan-5-yl | ethyl | $C_2H_5$ | $NH_2$ |
| 214 | 2-isopropyl-1,3-dioxepan-5-yl | ethyl | $C_2H_5$ | $NHCH_3$ |
| 215 | 2-isopropyl-1,3-dioxepan-5-yl | ethyl | $C_2H_5$ | $N(CH_3)_2$ |
| 216 | 2-isopropyl-1,3-dioxepan-5-yl | ethyl | $C_2H_5$ | 1-pyrrolidino |
| 217 | 2-isopropyl-1,3-dioxepan-5-yl | ethyl | $C_2H_5$ | $C_2H_5S$ |
| 218 | 2-isopropyl-1,3-dioxepan-5-yl | ethyl | $C_2H_5$ | 1-pyrazolyl |
| 219 | 2-isopropyl-1,3-dioxepan-5-yl | ethyl | $C_2H_5$ | 1,2,4-triazol-1-yl |
| 220 | 2-ethylthioprop-1-yl | ethyl | $C_2H_5$ | Cl |
| 221 | 2-ethylthioprop-1-yl | propyl | $C_2H_5$ | Cl |
| 222 | 2-ethylthioprop-1-yl | propyl | $C_2H_5$ | $NH_2$ |
| 223 | 2-ethylthioprop-1-yl | propyl | $C_2H_5$ | $N(CH_3)_2$ |
| 224 | 2-ethylthioprop-1-yl | propyl | $C_2H_5$ | N—morpholino |
| 225 | ethoxycarbonyl | propyl | $C_2H_5$ | Cl |
| 226 | ethoxycarbonyl | propyl | $C_2H_5$ | $NH_2$ |

TABLE 1-continued

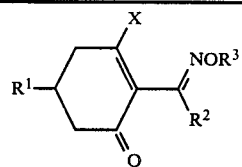

(Ib)

| Compound no. | R¹ | R² | R³ | X |
|---|---|---|---|---|
| 227 | ethoxycarbonyl | propyl | C₂H₅ | 1-pyrazolyl |
| 228 | ethoxycarbonyl | propyl | C₂H₅ | 1,2,4-triazol-1-yl |
| 370 | tetrahydropyran-4-yl | propyl | (E)—CH₂—CH=CH—Cl | |
| 371 | tetrahydropyran-4-yl | propyl | (E)—CH₂—CH=CH—Cl | N—morpholino |
| 372 | 6-methoxy-tetrahydropyran-3-yl | propyl | C₂H₅ | Cl |
| 373 | 3-isopropyl-isoxazol-5-yl | ethyl | C₂H₅ | NHCH₃ |

TABLE 2

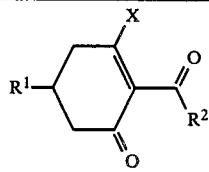

| Compound no. | R¹ | R² | X |
|---|---|---|---|
| 229 | tetrahydrofuran-2-yl | ethyl | Cl |
| 230 | tetrahydrofuran-2-yl | propyl | Cl |
| 231 | tetrahydrofuran-3-yl | ethyl | Cl |
| 232 | tetrahydrofuran-3-yl | propyl | Cl |
| 233 | tetrahydrofuran-3-yl | propyl | NH₂ |
| 234 | tetrahydrofuran-3-yl | propyl | NHCH₃ |
| 235 | tetrahydrofuran-3-yl | propyl | 1-pyrazolyl |
| 236 | tetrahydrofuran-3-yl | propyl | C₂H₅S |
| 237 | tetrahydrofuran-3-yl | ethyl | Cl |
| 238 | tetrahydrofuran-3-yl | propyl | Cl |
| 239 | 2,2-dimethyl-2,5-dihydrothien-3-yl | ethyl | Cl |
| 240 | 2,2-dimethyl-2,5-dihydrothien-3-yl | propyl | Cl |
| 241 | 2-furyl | ethyl | Cl |
| 242 | 2-furyl | propyl | Cl |
| 243 | 2-furyl | propyl | NH₂ |
| 244 | 2-furyl | propyl | 1-pyrrolidinyl |
| 245 | 2-furyl | propyl | N—morpholino |
| 246 | 2-furyl | propyl | phenylamino |
| 247 | 3-furyl | ethyl | Cl |
| 248 | 3-furyl | propyl | Cl |
| 249 | 2-thienyl | ethyl | Cl |
| 250 | 2-thienyl | propyl | Cl |
| 251 | 3-thienyl | ethyl | Cl |
| 252 | 3-thienyl | propyl | Cl |
| 253 | 2,5-dimethyl-thien-3-yl | ethyl | Cl |
| 254 | 2,5-dimethyl-thien-3-yl | propyl | Cl |
| 255 | 3-methyl-isoxazol-5-yl | ethyl | Cl |
| 256 | 3-methyl-isoxazol-5-yl | propyl | Cl |
| 257 | 3-isopropyl-isoxazol-5-yl | ethyl | Cl |
| 258 | 3-isopropyl-isoxazol-5-yl | propyl | Cl |
| 259 | 4-methyl-isothiazol-5-yl | ethyl | Cl |
| 260 | 4-methyl-isothiazol-5-yl | propyl | Cl |
| 261 | isothiazol-4-yl | ethyl | Cl |
| 262 | isothiazol-4-yl | propyl | Cl |
| 263 | 2-methyl-thiazol-4-yl | ethyl | Cl |
| 264 | 2-methyl-thiazol-4-yl | propyl | Cl |
| 265 | 2-methyl-thiazol-4-yl | ethyl | Cl |
| 266 | 2-methyl-thiazol-4-yl | propyl | Cl |
| 267 | 2-phenyl-thiazol-4-yl | ethyl | Cl |
| 268 | tetrahydropyran-2-yl | ethyl | Cl |
| 269 | tetrahydropyran-2-yl | propyl | Cl |
| 270 | 6-methyl-tetrahydropyran-2-yl | ethyl | Cl |
| 271 | 6-methyl-tetrahydropyran-2-yl | propyl | Cl |
| 272 | 6-methoxy-tetrahydropyran-2-yl | ethyl | Cl |
| 273 | 6-methoxy-tetrahydropyran-2-yl | propyl | Cl |
| 274 | 6-ethoxy-tetrahydropyran-2-yl | ethyl | Cl |
| 275 | 6-ethoxy-tetrahydropyran-2-yl | propyl | Cl |
| 276 | tetrahydropyran-3-yl | methyl | Cl |
| 277 | tetrahydropyran-3-yl | ethyl | Cl |

TABLE 2-continued

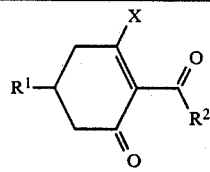

| Compound no. | R¹ | R² | X |
|---|---|---|---|
| 278 | tetrahydropyran-3-yl | propyl | Cl |
| 279 | tetrahydropyran-3-yl | propyl | $NH_2$ |
| 280 | tetrahydropyran-3-yl | propyl | $NHCH_3$ |
| 281 | tetrahydropyran-3-yl | propyl | $C_2H_5S$ |
| 282 | tetrahydropyran-3-yl | propyl | 1,2,4-triazol-1-yl |
| 283 | tetrahydropyran-3-yl | propyl | 1-pyrazolyl |
| 284 | tetrahydropyran-3-yl | propyl | 1-imidazolyl |
| 285 | tetrahydropyran-3-yl | propyl | N—piperidyl |
| 286 | tetrahydropyran-3-yl | propyl | N—morpholino |
| 287 | 4-methyl-tetrahydropyran-3-yl | ethyl | Cl |
| 288 | 4-methyl-tetrahydropyran-3-yl | propyl | Cl |
| 289 | 2-methoxy-tetrahydropyran-3-yl | ethyl | Cl |
| 290 | 2-methoxy-tetrahydropyran-3-yl | propyl | Cl |
| 291 | tetrahydropyran-4-yl | methyl | Cl |
| 292 | tetrahydropyran-4-yl | ethyl | Cl |
| 293 | tetrahydropyran-4-yl | propyl | Cl |
| 294 | tetrahydropyran-4-yl | isopropyl | Cl |
| 295 | tetrahydropyran-4-yl | Butyl | Cl |
| 296 | tetrahydropyran-4-yl | isobutyl | Cl |
| 297 | tetrahydropyran-4-yl | ethyl | $NH_2$ |
| 298 | tetrahydropyran-4-yl | ethyl | $NHCH_3$ |
| 299 | tetrahydropyran-4-yl | ethyl | $N(CH_3)_2$ |
| 300 | tetrahydropyran-4-yl | ethyl | phenylamino |
| 301 | tetrahydropyran-4-yl | ethyl | isopropylamino |
| 302 | tetrahydropyran-4-yl | ethyl | 1-pyrrolidinyl |
| 303 | tetrahydropyran-4-yl | ethyl | $C_2H_5S$ |
| 304 | tetrahydropyran-4-yl | ethyl | 1-pyrazol |
| 305 | tetrahydropyran-4-yl | ethyl | 1,2,4-triazol-1-yl |
| 306 | 3-methyl-tetrahydropyran-4-yl | ethyl | Cl |
| 307 | 3-methyl-tetrahydropyran-4-yl | propyl | Cl |
| 308 | $\Delta^3$-dihydropyran-3-yl | ethyl | Cl |
| 309 | $\Delta^3$-dihydropyran-3-yl | propyl | Cl |
| 310 | tetrahydrothiopyran-3-yl | methyl | Cl |
| 311 | tetrahydrothiopyran-3-yl | ethyl | Cl |
| 312 | tetrahydrothiopyran-3-yl | propyl | Cl |
| 313 | tetrahydrothiopyran-3-yl | isopropyl | Cl |
| 314 | tetrahydrothiopyran-3-yl | butyl | Cl |
| 315 | tetrahydrothiopyran-3-yl | isobutyl | Cl |
| 316 | tetrahydrothiopyran-3-yl | propyl | F |
| 317 | tetrahydrothiopyran-3-yl | propyl | Br |
| 318 | tetrahydrothiopyran-3-yl | propyl | $NH_2$ |
| 319 | tetrahydrothiopyran-3-yl | propyl | $NHCH_3$ |
| 320 | tetrahydrothiopyran-3-yl | propyl | $N(CH_3)_2$ |
| 321 | tetrahydrothiopyran-3-yl | propyl | $CH_3S$ |
| 322 | tetrahydrothiopyran-3-yl | propyl | $C_2H_5S$ |
| 323 | tetrahydrothiopyran-3-yl | propyl | $n-C_3H_7S$ |
| 324 | tetrahydrothiopyran-3-yl | propyl | phenylthio |
| 325 | tetrahydrothiopyran-3-yl | propyl | 1-pyrazolyl |
| 326 | tetrahydrothiopyran-3-yl | propyl | 1,2,4-triazol-1-yl |
| 327 | 1-oxo-tetrahydrothiopyran-3-yl | ethyl | Cl |
| 328 | 1-oxo-tetrahydrothiopyran-3-yl | propyl | Cl |
| 329 | 1,1-dioxo-tetrahydrothiopyran-3-yl | ethyl | Cl |
| 330 | 1,1-dioxo-tetrahydrothiopyran-3-yl | propyl | Cl |
| 331 | tetrahydrothiopyran-4-yl | ethyl | Cl |
| 332 | tetrahydrothiopyran-4-yl | propyl | Cl |
| 333 | $\Delta^3$-dihydrothiopyran-3-yl | ethyl | Cl |
| 334 | $\Delta^3$-dihydrothiopyran-3-yl | propyl | Cl |
| 335 | 5,5-dimethyl-1,3-dioxan-2-yl | ethyl | Cl |
| 336 | 5,5-dimethyl-1,3-dioxan-2-yl | propyl | Cl |
| 337 | 1,4-dioxan-2-yl | ethyl | Cl |
| 338 | 1,4-dioxan-2-yl | propyl | Cl |
| 339 | 1,4-dithian-2-yl | ethyl | Cl |
| 340 | 1,4-dithian-2-yl | propyl | Cl |
| 341 | 2-pyridyl | ethyl | Cl |
| 342 | 2-pyridyl | propyl | Cl |
| 343 | 3-pyridyl | ethyl | Cl |
| 344 | 3-pyridyl | propyl | Cl |
| 345 | 3-pyridyl | propyl | $NH_2$ |
| 346 | 3-pyridyl | propyl | $N(CH_3)_2$ |
| 347 | 3-pyridyl | propyl | 1-pyrazolyl |
| 348 | 3-pyridyl | propyl | 1,2,4-triazol-1-yl |

TABLE 2-continued

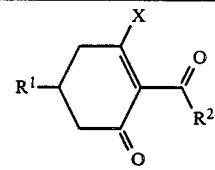

| Compound no. | R¹ | R² | X |
|---|---|---|---|
| 349 | 1,3-dioxepan-5-yl | ethyl | Cl |
| 350 | 1,3-dioxepan-5-yl | propyl | Cl |
| 351 | 2-methyl-1,3-dioxepan-5-yl | ethyl | Cl |
| 352 | 2-methyl-1,3-dioxepan-5-yl | propyl | Cl |
| 353 | 2-isopropyl-1,3-dioxepan-5-yl | ethyl | Cl |
| 354 | 2-isopropyl-1,3-dioxepan-5-yl | ethyl | $NH_2$ |
| 355 | 2-isopropyl-1,3-dioxepan-5-yl | ethyl | $NHCH_3$ |
| 356 | 2-isopropyl-1,3-dioxepan-5-yl | ethyl | $N(CH_3)_2$ |
| 357 | 2-isopropyl-1,3-dioxepan-5-yl | ethyl | 1-pyrrolidino |
| 358 | 2-isopropyl-1,3-dioxepan-5-yl | ethyl | $C_2H_5S$ |
| 359 | 2-isopropyl-1,3-dioxepan-5-yl | ethyl | 1-pyrazolyl |
| 360 | 2-isopropyl-1,3-dioxepan-5-yl | ethyl | 1,2,4-triazol-1-yl |
| 361 | 2-ethylthioprop-1-yl | ethyl | Cl |
| 362 | 2-ethylthioprop-1-yl | propyl | Cl |
| 363 | 2-ethylthioprop-1-yl | propyl | $NH_2$ |
| 364 | 2-ethylthioprop-1-yl | propyl | $N(CH_3)_2$ |
| 365 | 2-ethylthioprop-1-yl | propyl | N—morpholino |
| 366 | ethoxycarbonyl | propyl | Cl |
| 367 | ethoxycarbonyl | propyl | $NH_2$ |
| 368 | ethoxycarbonyl | propyl | 1-pyrazolyl |
| 369 | ethoxycarbonyl | propyl | 1,2,4-triazol-1-yl |
| 374 | tetrahydrothiopyran-3-yl | propyl | pyrrolidinyl |
| 375 | 1-oxo-tetrahydrothiopyran-3-yl | propyl | pyrrolidinyl |
| 376 | 1,1-dioxo-tetrahydrothiopyran-3-yl | propyl | pyrrolidinyl |
| 377 | ethoxycarbonyl | propyl | $N(CH_3)_2$ |
| 378 | ethoxycarbonyl | propyl | $NH_2$ |
| 379 | ethoxycarbonyl | propyl | $n-C_3H_7-S$ |
| 380 | ethoxycarbonyl | propyl | $NH-CH(CH_3)_2$ |

The compounds of the formula I are identified and characterized best with the aid of proton resonance spectroscopy. The table below contains some structure-specific $^1$H-NMR data (solvent: CDCl$_3$, internal standard: tetramethylsilane; s=singlet, d=doublet, t=triplet, q=quartet, m=multiplet).

| Compound no. | Characteristic $^1$H-NMR data (S) in ppm |
|---|---|
| 22 | 0.97(t); 4.17(q); 6.87(d); 6.98(dd); 7.22(d) |
| 29 | 0.92(t); 1.27(m); 4.17(q); 5.95(s) |
| 53 | 0.92(t); 1.26(t); 3.88(t); 4.14(q) |
| 71 | 0.96(t); 3.38(t); 4.01(d); 4.59(d) |
| 73 | 1.13(t); 2.93(s); 3.99(m); 4.50(d); 6.28(d) |
| 74 | 1.07(t); 2.98(s); 3.40(t); 4.59(d); 6.30(d) |
| 76 | 1.07(t); 1.24(t); 3.39(t); 4.55(d); 6.26(d) |
| 77 | 1.03(t); 3.33(m); 4.01(d); 4.56(d); 6.26(d) |
| 90 | 0.97(t); 1.30(t); 2.0–3.0(m)(t); 4.20(q) |
| 93 | 0.89(t); 1.23(t); 4.12(q) |
| 94 | 0.88(t); 1.25(t); 2.95(d); 4.07(q) |
| 95 | 0.92(t); 1.26(t); 2.95(s); 4.13(q) |
| 96 | 0.92(t); 2.42(s); 4.05(q,anti); 4.15(q,syn) |
| 101 | 0.93(t); 3.42(m); 4.13(q); |
| 102 | 0.92(t); 3.33(m); 3.70(t); 4.14(q) |
| 103 | 0.95(t); 3.78(m); 4.08(q); 8.32(NH) |
| 122 | 0.92(t); 1.71(d); 4.5(m); 5.67(m) |
| 170 | 0.93(t); 1.40(m); 4.67(s) |
| 221 | 0.92(m); 2.82(m); 4.14(q); 4.14(q) |
| 225 | 0.92(t); 2.42(m); 4.17(2q) |
| 250 | 1.13(t); 3.78(m); 6.88(s); 6.97(dd); 7.22(d) |
| 292 | 1.13(t); 3.77(t); 4.02(q) |
| 297 | 1.04(t); 2.97(m); 3.37(t); 4.01(d) |
| 298 | 1.07(t); 3.05(d); 3.37(t); 4.02(d) |
| 299 | 1.03(t); 3.02(s); 3.37(t); 4.00(d) |
| 301 | 1.07(t); 1.32(t); 3.38(t); 3.87(m); 4.02(d) |
| 302 | 1.07(t); 3.37(t); 3.98(d) |
| 304 | 1.17(t); 3.42(t); 4.04(d); 6.45(s); 7.67(s); 7.73(dd) |
| 305 | 1.14(t); 3.43(t); 8.04(s); 8.47(s) |

-continued

| Compound no. | Characteristic $^1$H-NMR data (S) in ppm |
|---|---|
| 310 | 1.27(m); 1.62(m); 2.37(s); 3.89(t) |
| 312 | 0.98(t); 1.23(m); 1.5–2.9(m); |
| 318 | 0.97(t); 2.93(m); 6.18(s); 11.19(s) |
| 319 | 0.95(t); 2.95(t); 3.10(NCH$_3$); 12.5(s) |
| 320 | 0.95(t); 1.55–2.95(m); 3.04(s) |
| 323 | 0.98(t); 1.06(t); 2.0–3.0(m); |
| 324 | 1.01(t); 2.81(t); 7.45(m) |
| 325 | 0.96(t); 3.08(d); 6.47(s); 7.68(s); 7.78(s) |
| 326 | 0.96(t); 3.07(d); 8.06(s); 8.48(s) |
| 367 | 0.92(t); 1.25(t); 1.60(m); 4.19(q) |
| 368 | 0.92(t); 1.28(t); 4.22(q); 6.46(m); 6.68(d); 7.77(d) |
| 369 | 0.95(t); 1.26(t); 2.58(t); 8.05(s); 8.51(s) |
| 330 | 0.95(t); 1.68(q); 2.58(t) |
| 370 | 0.90(t); 3.38(t); 4.57(d) |
| 371 | 0.95(t); 4.59(d); 6.31(d) |
| 372 | 0.92(t); 1.26(t); 3.37(s); 4.14(q) |
| 373 | 1.01(t); 4.09(q); 5.96(s) |
| 374 | 0.95(t); 2.2–2.8(m); 2.9–3.05(m) |
| 375 | 0.96(t); 1.1–3.8(m) |
| 377 | 0.94(t); 1.27(t); 3.03(s) |
| 378 | 0.92(t); 1.25(t); 1.60(m); 4.19(q) |
| 379 | 0.97(t); 1.08(t); 1.31(t); 4.23(q) |
| 380 | 0.95(t); 1.36(d); 4.18(q) |

The cyclohexanone derivatives of the formula I may be applied for instance in the form of directly sprayable solutions, powders, suspensions (including high-percentage aqueous, oily or other suspensions), dispersions, emulsions, oil dispersions, pastes, dusts, broadcasting agents or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, and paraffin, tetrahydrocarbons such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts of sulfated fatty alcohol glycol ethers, condensation products of sulfonated naphthalene and naphthalene derivatives with formaldehyde, condensation products of naphthalene or naphthalenesulfonic acids with phenol or formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxy propylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate and ureas, and vegetable products such as grain flours, bark meal, wood meal and nutshell meal, cellulosic powders, etc.

The formulations contain from 0.1 to 95, and preferably from 0.5 to 90, % by weight of active ingredient.

Examples of formulations are given below.

I. 90 parts by weight of compound no. 71 is mixed with 10 parts by weight of N-methyl-α-pyrrolidone. A mixture is obtained which is suitable for application in the form of very fine drops.

II. 20 parts by weight of compound no. 102 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of active ingredient.

III. 20 parts by weight of compound no. 90 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of active ingredient.

IV. 20 parts by weight of compound no. 53 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of active ingredient.

V. 20 parts by weight of compound no. 310 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of active ingredient.

VI. 3 parts by weight of compound no. 366 is intimately mixed with 97 parts by weight of particulate kaolin. A dust is obtained containing 3% by weight of active ingredient.

VII. 30 parts by weight of compound no. 325 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 310 is intimately mixed with 2 parts by weight of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

IX. 40 parts by weight of compound no. 53 is dissolved in 60 parts by weight of a mixture consisting of 93 wt% of xylene and 7 wt% of the adduct of 8 moles of ethylene oxide and 1 mole of nonylphenol. A solution is obtained containing 40 wt% of the active ingredient.

The novel cyclohexenone derivatives of the formula I in which A is $NOR^3$ have a good herbicidal action, particularly on species from the Gramineae family. They are tolerated by, and are thus selective in, broad-leaved crops and monocotyledons not belonging to the Gramineae. Some of the novel compounds are selective in graminaceous crops such as wheat and rice, and at the same time combat unwanted grasses. The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (postdirected, lay-by treatment).

The amounts of active ingredient applied depends on the time of the year, the plants to be combated and their growth stage, and varies from 0.025 to 3 kg/ha, but is preferably from 0.05 to 1.0 kg/ha.

The action of the cyclohexenone derivatives of the formula I (A=NOR$^3$) on plant growth is demonstrated in greenhouse experiments.

The vessels employed were plastic flowerpots having a volume of 300 cm$^3$, and which were filled with a sandy loam containing about 3.0% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. The application rates for postemergence treatment were from 0.5 to 1.0 kg of active ingredient per hectare. No covers were placed on the vessels in this method.

The pots were set up in the greenhouse-species from warmer areas at from 20° C. to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plant species used in the greenhouse experiments were *Alopecurus myosuroides, Avena sativa, Glycine max, Lolium multiflorum, Setaria italica, Sinapis alba, Zea mays, Avena fatua, Digitaria sanguinalis, Echinochloa crus-galli, Medicago sativa*, and *Triticum aestivum*.

Plants from the Gramineae family were well combated with preemergence applications of 3 kg/ha of compounds nos. 90, 102 and 71 selected by way of example. Mustard, as an example of a broadleaved crop plant, suffered no damage whatsoever.

On postemergence application, for instance compounds nos. 53 and 90 are suitable for combating unwanted grass growth; volunteer crop plants such as Indian corn are also combated. The broadleaved crop plant soybeans remains completely unaffected.

Postemergence, for example compounds nos. 71 and 102 are suitable, at a rate of 1 kg/ha, for combating grasses without causing damage to the crop plant alfalfa.

On postemergence application of 0.5 kg/ha, for instance compounds nos. 212 and 371 destroyed *Setaria italica, Digitaria sanguinalis* and *Echinochloa crus-galli*, whereas wheat remained almost undamaged.

Compound no. 122, at a rate of, for example, 1 kg/ha, caused heavy damage to unwanted grasses, the crop plant alfalfa remaining unaffected.

At an application rate of 3 kg/ha, for example compounds nos. 71, 96, 102, 122 and 371 caused heavy damage to grass species; the broadleaved crop plant mustard remained undamaged.

In view of the spectrum of weeds which can be combated, the tolerance of the active ingredients according to the invention by crop plants, the desired influence on the growth of crop plants, and in view of the numerous application methods possible, the compounds of the formula I according to the invention (A=NOR$^3$) may be used in a large number of crop plants.

To increase the spectrum of action and to achieve synergistic effects, the cyclohexenone derivatives of the formula I (A=NOR$^3$) may be mixed and applied together with numerous representatives of other herbicidal or growth-regulating active ingredient groups. Examples or suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acid derivatives, etc.

It may also be useful to apply the cyclohexenone derivatives of the formula I (A=NOR$^3$), either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

The cyclohexenone derivatives of the formula I (A=oxygen) may have a variety of influences on practically all plant development stages, and may therefore be used as growth regulators. The diversity of action of growth regulators depends especially on (a) the type and variety of plant;

(b) the time applied, with reference to the development stage of the plants and the time of the year;

(c) the place and method of application (seed treatment, soil treatment, or application to foliage);

(d) climatic factors, e.g., temperature, amount of precipitate, day length and light intensity;

(e) soil conditions (including fertilization);

(f) the formulation of the active ingredient; and (g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The cyclohexenone derivatives of the formula I (A=oxygen) may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia,
the size of the stomata opening is reduced;
a thicker epidermis and cuticle are formed;
penetration of the soil by the roots is improved;
the micro-climate in the stand is favorably influenced by the more compact growth.

The active ingredients of the formula I to be used in accordance with the invention (A=oxygen) may be applied not only to the seed (as a disinfectant), but also to the soil, i.e., via the roots, and—the method particularly preferred—to the foliage by spraying.

As a result of the good crop plant tolerance, the application rate may vary considerably. When seed is treated, active ingredient amounts of from 0.001 to 50, and preferably from 0.01 to 10, g per kg of seed are generally needed. When the soil or foliage is treated, rates of from 0.01 to 10, and preferably from 0.05 to 3, kg per hectare are generally considered to be sufficient.

To determine the growth-regulating properties of the candidate compounds, a culture medium was supplied with sufficient nutrients, and test plants were grown therein in plastic pots approx. 12.5 cm in diameter.

For the preemergence treatment, the candidate compounds were applied as aqueous formulations to the seedbed on the day of sowing.

Postemergence, the candidate compounds were sprayed as aqueous formulations onto the plants. The growth-regulating action observed was confirmed at the end of the experiment by measuring the growth height. The figures obtained were compared with those for untreated plants. Chlorocholine chloride was used for comparison purposes.

Not only was growth height reduced—the leaves also took on a more intense color. The increased chlorophyll content is indicative of a higher rate of photosynthesis, making for bigger yields.

Compounds nos. 310, 325 and 366 selected by way of example exhibited significant growth-regulating properties on postemergence application.

The growth-regulating agents according to the invention may, in the above-mentioned application forms, be mixed and applied together with other active ingredients, such as herbicides, insecticides, other growth regulators and fungicides, or with fertilizers. When the compounds according to the invention are mixed with other growth regulators, synergistic effects occur, i.e., the effectiveness of the combination is greater than the added actions of the individual components.

Examples of fungicides which may be admixed with the novel compounds of the formula I (A=oxygen) are as follows:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and N,N'-polypropylenebis(thiocarbamyl)disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[bis-(dimethylamino)-phosphinyl]-3-phenyl-1,2,4-triazole,
2,3-dicyano-1,4-dithiaanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiin,
2,3-dihydro-5-carboxanilido-6-methyl-1,4-oxathiin 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-dimethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolylurea,
1-(4-chlorophenoxy)-3,3-dimethyl-1-(1H-1,2,4-triazol-1-yl)butan-2-one,
1-(4-chlorophenoxy)-3,3-dimethyl-1-(1H-1,2,4-triazol-1-yl)butan-2-ol,
α-(2-chlorophenyl)-α-(4-chlorophenyl)-5-pyrimidinemethanol,
5-butyl-2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and
various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole, and
2,4-difluoro-α-(1H-1,2,4-triazol-1-ylmethyl)-benzhydryl alcohol.

We claim:

1. A cyclohexenone derivative of the formula

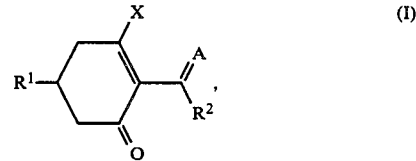

where
R$^1$ is a 5-, 6- or 7-membered heterocycle of 1, 2 or 3 sulfur hetero ring members, which may contain 1, 2 or 3 double bonds and up to 3 substituents selected from the group consisting of C$_1$–C$_6$-alkyl, C$_2$–C$_6$-alkenyl, C$_1$–C$_6$-alkoxy, C$_1$–C$_6$-alkylthio, C$_1$–C$_4$-dialkylamino and C$_2$–C$_8$-alkoxyalkyl, or is 2-ethylthiopropyl or C$_1$–C$_6$-alkoxycarbonyl, R$^2$ is C$_1$–C$_4$-alkyl, A is NOR$^3$, where R$^3$ is C$_1$–C$_4$-alkyl, C$_3$–C$_4$-alkenyl, C$_3$-alkynyl, C$_4$-alkynyl, C$_2$–C$_4$-haloalkyl, C$_3$–C$_4$-haloalkenyl or C$_2$–C$_4$-alkoxyalkyl, and X is halogen, or C$_1$–C$_4$-alkylthio, phenylthio.

* * * * *